United States Patent [19]
Lund et al.

[11] Patent Number: 5,111,696
[45] Date of Patent: May 12, 1992

[54] METHOD OF VISUALIZING REFLECTION CHARACTERISTIC IN ULTRASONIC EXAMINATION

[75] Inventors: Svend A. Lund, Birkerød; Bent E. Nielsen, Lyngby, both of Denmark

[73] Assignee: Akademiet For De Tekniske Videnskaber, Svejsecentralen, Brondby, Denmark

[21] Appl. No.: 602,046

[22] Filed: Oct. 24, 1990

Related U.S. Application Data

[63] Continuation of Ser. No. 300,934, Jan. 24, 1989, abandoned.

[51] Int. Cl.$^5$ .................. G01N 9/24; G06F 15/20
[52] U.S. Cl. ........................ 73/627; 73/602; 364/507
[58] Field of Search ............ 73/602, 620, 627, 618, 73/629; 364/506, 507

[56] References Cited

U.S. PATENT DOCUMENTS

| | | | |
|---|---|---|---|
| 3,673,860 | 7/1972 | Flaherty et al. | 73/620 |
| 3,857,052 | 12/1974 | Beller | 340/149 |
| 3,939,697 | 2/1976 | Lund et al. | 73/614 |
| 3,962,909 | 6/1976 | Lund | 73/620 |
| 4,010,634 | 3/1977 | Baumgartner | 73/620 |
| 4,226,122 | 10/1980 | Lund et al. | 73/609 |
| 4,292,848 | 10/1981 | Rainey et al. | 73/602 |
| 4,441,369 | 4/1984 | Lessard et al. | 73/620 |
| 4,481,822 | 11/1984 | Kubota et al. | 73/625 |
| 4,495,816 | 1/1985 | Schlumberger | 73/600 |
| 4,531,409 | 7/1985 | Koch et al. | 73/588 |
| 4,597,292 | 7/1986 | Fujii et al. | 73/599 |
| 4,742,713 | 5/1988 | Abe et al. | 73/620 |
| 4,908,774 | 3/1990 | Lund | 364/507 |

OTHER PUBLICATIONS

IEEE Transactions on Sonics and Ultrasonics, vol. SU-32, No. 4, Jul., 1985, pp. 531-536.
Computer Simulation of Ultrasonics in a Solid, NDT International, vol. 19, No. 6, Oct. 1986, pp. 315-332.

*Primary Examiner*—Hezron E. Williams
*Assistant Examiner*—Louis M. Arana
*Attorney, Agent, or Firm*—Banner, Birch, McKie & Beckett

[57] ABSTRACT

A prior art computerized ultrasonic examination is performed by moving an ultrasonic probe over the surface of an object, transmitting short pulses of ultrasonic energy into the material. Combined digital position and echo pulse signals are electronically stored, processed, and used for the display of a first video sectional flaw image of a selected sectional plane through the object. Representatives of reflected echo amplitudes from a chosen location are now shown, either in said first flaw image, or in at least one separate sectional view, as lengths of line segments originating at an image pixel representing said location, and drawn in the directions of the projections on said selected sectional plane of the incoming pulses at said location. In typical examples it is demonstrated, how reflected waves can be visualized and evaluated, and how the corresponding flaw images can be superimposed on said first video flaw image, thereby adding important information which is normally disregarded in the prior art. This visualization can be made on line during the examination or in later post processing and closer analysis of the results of the examination.

26 Claims, 6 Drawing Sheets

PRIOR ART

METHOD OF VISUALIZING REFLECTION CHARACTERISTIC IN ULTRASONIC EXAMINATION

This application is a continuation of application Ser. No. 07/300,934, filed Jan. 24, 1989 now abandoned.

BACKGROUND OF THE INVENTION

1. Field of the invention

This invention relates to the analysis and evaluation of the results of ultrasonic examinations of solid objects by the pulse-echo method. The correct location, interpretation and sizing of internal flaws in materials and welded joints are matters of the greatest importance for the safety and fitness for purpose of important structures and installations.

2. Background of the Prior Art

In the ultrasonic examination art, great efforts have been made to develop improved systems for the location and sizing of flaws in materials and welded joints, in particular systems producing easily readable images of internal flaws. In many systems this has been made possible through the use of digital computing means including electronic matrix memories for the storage of echo data which may then be analysed, displayed on video monitors as grey scale or colour images, and permanently recorded by magnetic recording means or permanent prints.

In two previous patent applications, WO Lund et al. 87/07026, and U.S. Lund et al. Ser. No. 223,014, filed Apr. 1988 we have disclosed systems and methods of ultrasonic examination providing sectional and projection views showing flaw images of greatly improved precision and sharpness of definition.

According to said previous inventions, at least one ultrasonic probe is moved over the surface of the object examined, transmitting, at predetermined intervals of time, at least one short pulse of ultrasonic energy into the object. Signals containing information on the points of incidence of the sound beam, on the directions of the central axis of the sound beam, on the amplitudes of echo pulses from inhomogeneities, and on the corresponding path lengths of the sound beam, are measured, digitalised, stored and used to create video sectional and projection views showing clear and sharp images of inhomogeneities inside the object. Such images may then be permanently recorded and printed in grey scale and colours for display, analysis and evaluation at any later time. The systems according to said previous inventions have, in practical examinations, led to a drastic increase in the quality and precision of sectional and projection images, permitting a correct and precise location and evaluation of all inhomogeneities in three dimensions.

One problem has, however, remained to be solved. When a sound pulse is transmitted into the material and reflected from an inhomogeneity, the sound may travel along several different paths and undergo mode conversion on its way to and from the inhomogeneity. This fact leads to the formation of multiple images of one and the same inhomogeneity, and to 'ghost images' due to reflections from other inhomogeneities. It is then a cumbersome and time consuming task to keep track of and evaluate or eliminate such echoes, before a final decision can be made on the correct interpretation of the results of the examination.

SUMMARY OF THE INVENTION

The method according to the present invention has been evolved with the object of overcoming the disadvantages of the prior art by providing a new and satisfactory method of interpretation and evaluation of the results of ultrasonic examinations which have produced complex and overlapping patterns of flaw images.

According to the present invention a method is disclosed of visualising reflection characteristics of reflecting inhomogeneities located by pulse-echo examinations of an otherwise homogeneous object, by showing representatives of the echo amplitudes from a chosen location in a video image of a sectional plane through the object as lengths of line segments, originating at an image pixel representing said location, and drawn in the directions of the projections on said sectional plane of the incoming ultrasonic pulses at said location.

By the method disclosed, it has become possible to create clearly visible images of all the various echo amplitudes originating at a chosen location, thereby greatly facilitating the task of interpretation and making use of all significant echoes, and eliminating echoes representing false reflections.

According to a first method of realising the invention, at least one ultrasonic probe is moved over the surface of the object, transmitting at predetermined intervals of time at least one short pulse of ultrasonic energy into the object and receiving echo pulses from internal inhomogeneities, where digital computing means are adapted to store digital signals containing information on the corresponding successive positions of the point of incidence and directions of the central axis of the sound beam, and, on receipt of an echo pulse, information on the amplitude of said echo pulse, and on the length of the sound path from said point of incidence to the reflecting point causing the echo pulse, and where said digital signals are used to display a video image of a sectional plane through the object by showing said line segments superimposed on said video sectional image.

By this method all useful echoes which have been stored during the examination may be clearly indicated, originating from the point in the image where an inhomogeneity has been located, making it easy to see, understand and evaluate echoes which are important to the correct interpretation of the image of the inhomogeneity under consideration.

According to a second method of realising the invention, the same steps are taken as described above, but in this case the line segments indicating echo amplitudes are shown in at least one separate video sectional image, where the chosen image pixel is placed at the centre of the image, and where said line segments are drawn in the directions corresponding to the projections on said sectional plane of the incoming ultrasonic pulses at said location.

In this case the visualising of the flaw echoes is performed separately in one or more echo amplitude images which may be permanently recorded and/or printed out for further study, while the corresponding flaw images are superimposed on the original video sectional image.

According to the second method described above it becomes possible to exemplify the application of the invention in specific characteristic situations, and 12 such typical situations, covering objects having two plane and parallel surfaces, have been described in more detail. For someone well versed in the art of ultrasonic examinations, it will be easy to extend these descriptions to cover also the use of double probes, tandem probes, or multiarray probes, as well as the examination of T-joints, clad steels, pipe connections and even more complex situations, where the invention will equally facilitate the interpretation and evaluation of the results.

Other objects and advantages of the invention will be readily apparent from the following description taken in conjunction with the accompanying drawings.

DETAILED DESCRIPTION OF THE ILLUSTRATED EMBODIMENTS

Figure 1:
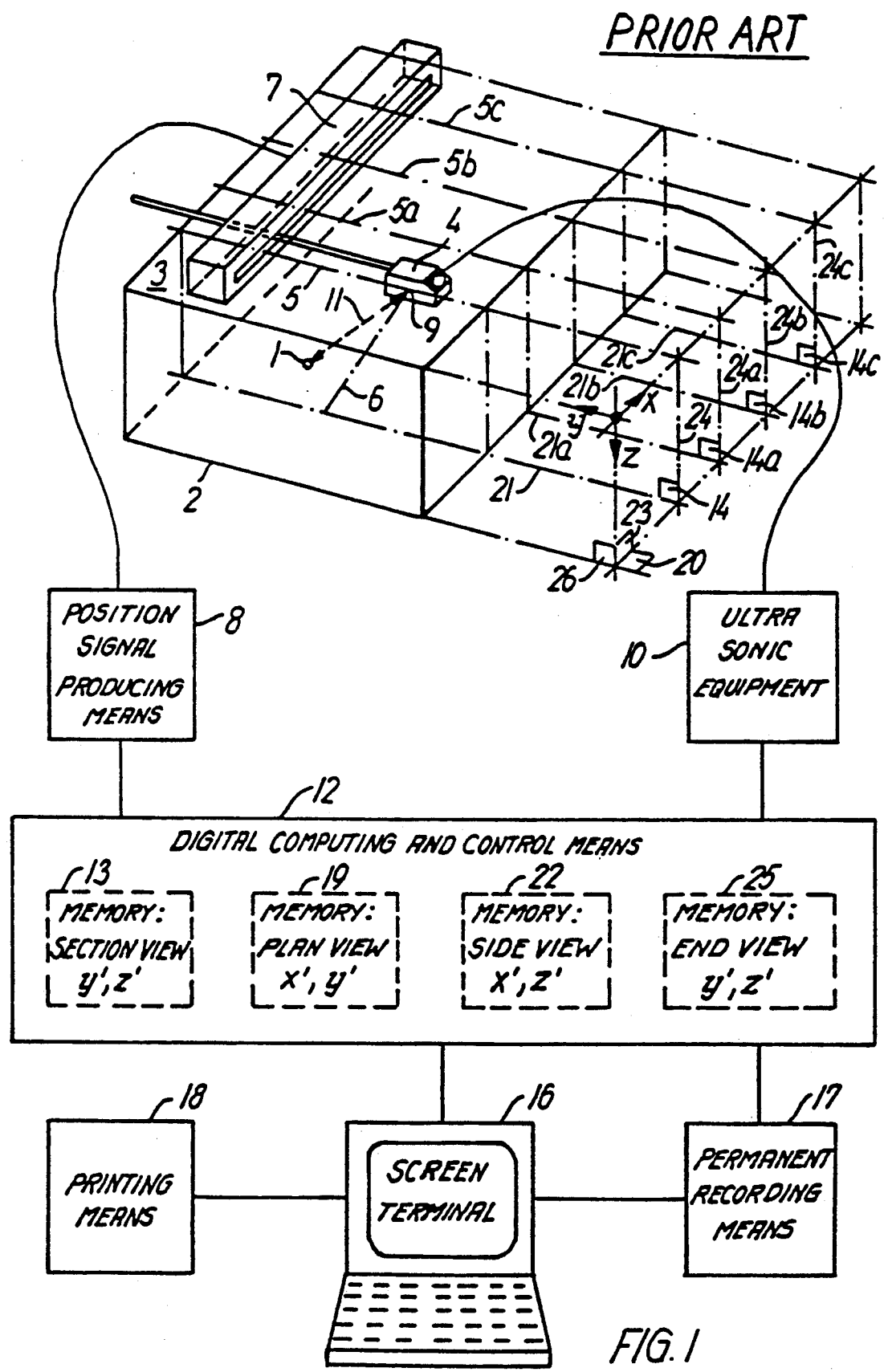
FIG. 1 is a schematic presentation partly as an isometric view, and partly as a block diagram, of a prior art ultrasonic examination system, constituting the background of the present invention.

FIG. 1 shows schematically a prior art ultrasonic system and method for producing and recording images of inhomogeneities 1 in an object 2 having a plane surface 3. An ultrasonic probe 4 is moved along a scanning path 5, transmitting short pulses of ultrasonic energy into the object in a sound beam having a central axis 6. Position signal producing means 7, 8 is adapted to transmit digital signals containing information on the positions of successive points of incidence 9 and directions of the axis 6 in a system of co-ordinates (x,y,z) in fixed relation to the object. On receipt of an echo pulse, an ultrasonic equipment 10 produces digital echo signals containing information on the amplitude of the echo pulse, and on the length of the sound path 11 from the point of incidence 9 to the reflecting point 1.

Connected position and echo pulse signals are carried to digital computing and control means 12 including one or more electronic matrix memories 13, 19, 22, 25 for data produced by the examination. A video screen terminal 16 controls the scanning movement of the ultrasonic probe and the functioning of the ultrasonic equipment and the digital computing and control means 12, and displays images derived from data stored in the matrix memories 13,19,22,25. Recording means 17 is provided for producing permanent, electronically readable records of the data stored in the matrix memories and of images displayed on the screen terminal 16. Printing means 18 is provided for producing permanent prints of images displayed on the screen terminal.

Figure 2:
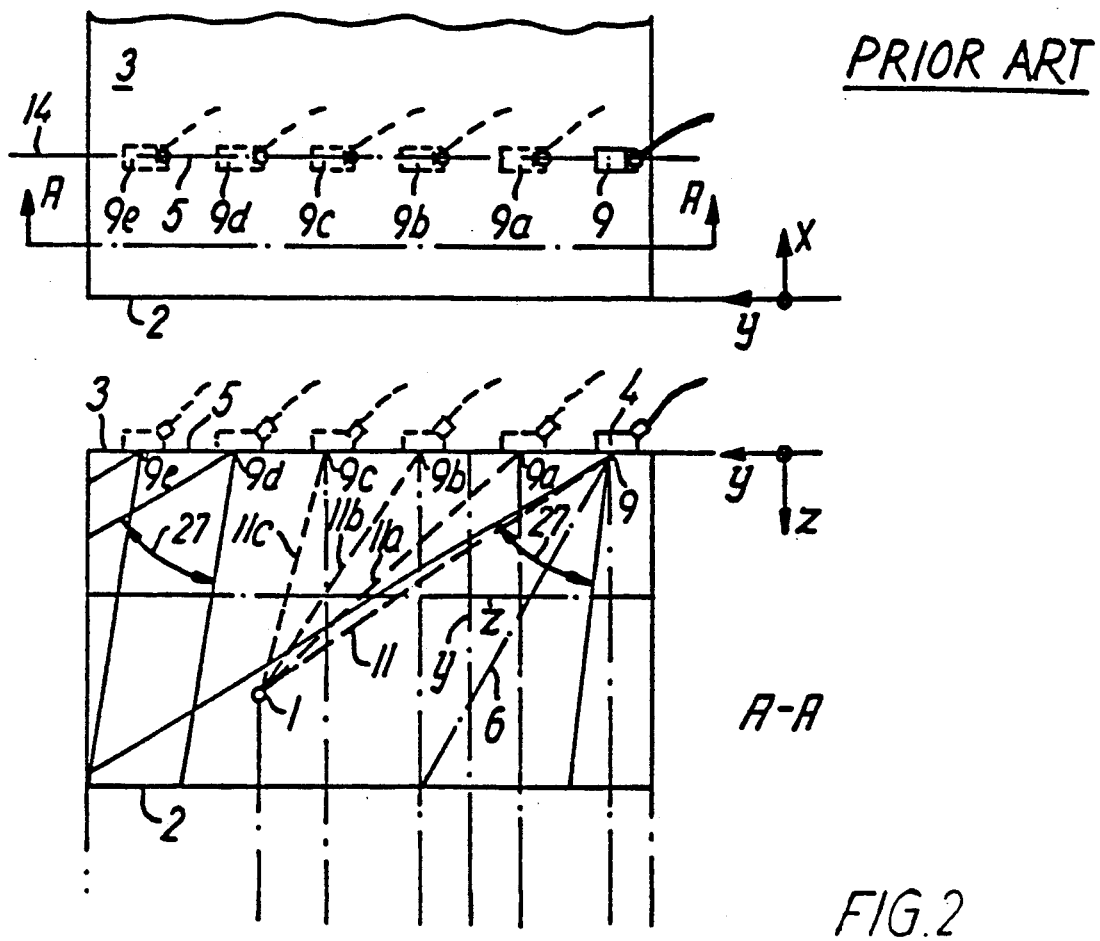
FIG. 2 is a schematic presentation of the production of a video sectional image (B-scan presentation) by means of the prior art system of FIG. 1.

FIG. 2 further illustrates schematically the operation of the prior art examination system when producing an image (B-scan display) of a sectional plane 14 through the object 2. The probe 4 is moved over the surface of the object to successive positions 9,9a,9b, . . . 9e. For each position, data representing echo pulse amplitudes, if any, are stored and used to display a normal complete sectional image on the video screen terminal 16.

It should be noted that the plane surface 3 is only shown as an example. In principle, the surface may have any shape, e.g. cylindrical or spherical, if only the shape of the surface is geometrically well defined in relation to the co-ordinates (x,y,z), and the digital computing and control means have been programmed accordingly.

Figure 3:
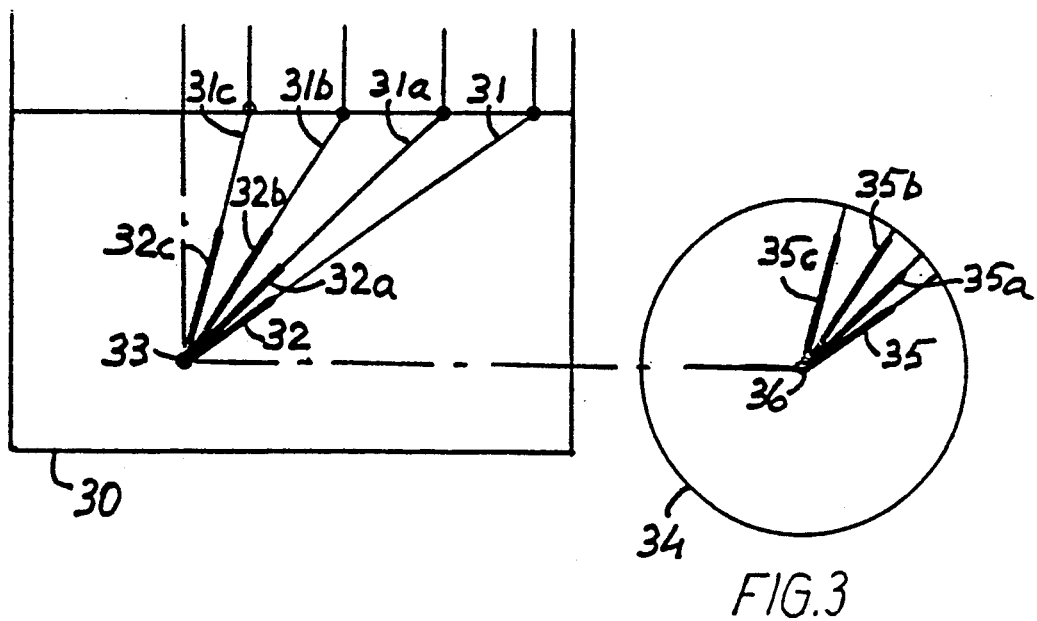
FIG. 3 is a schematic presentation of the video sectional image obtained in FIG. 2, but showing in accordance with the invention echo amplitude line segments, partly superimposed on the sectional image itself, and partly as an additional sectional image.

The inhomogeneity 1 present in the object of FIG. 1 is shown at 33 in the sectional image 30 in FIG. 3. FIG. 3 further shows the superimposed images of line segments 32,32a,32b,32c, in accordance with the present invention, indicating the echo amplitude values obtained in the corresponding positions 9,9a,9b, 9c of the ultrasonic probe, and the same amplitude values 35,35a,35b,35c from a selected image pixel 36, are further shown in a separate sectional image 34. The line segments may be shown as heavy lines in a separate colour, while the sound paths may be indicated by the thin lines 31,31a,31b,31c.

Each time an image pixel is selected for study, a search is started through the complete storage of echo amplitude values. For each distance 11,11a,11b, 11c a search is carried out among the stored values, and if an echo is found at the distance searched for, it is displayed as a line segment in the sectional image 30 and/or 34, and the corresponding flaw image 33 is shown superimposed on the sectional image 30.

It is clearly seen, how the amplitude line segments can be of great help in evaluating the results of the examination. Each type of inhomogeneity displays an individual pattern of echo amplitudes, e.g. plane defects at right angles to the defect plane, while inclusions have a tendency to reflect uniformly in all directions.

Figure 4:
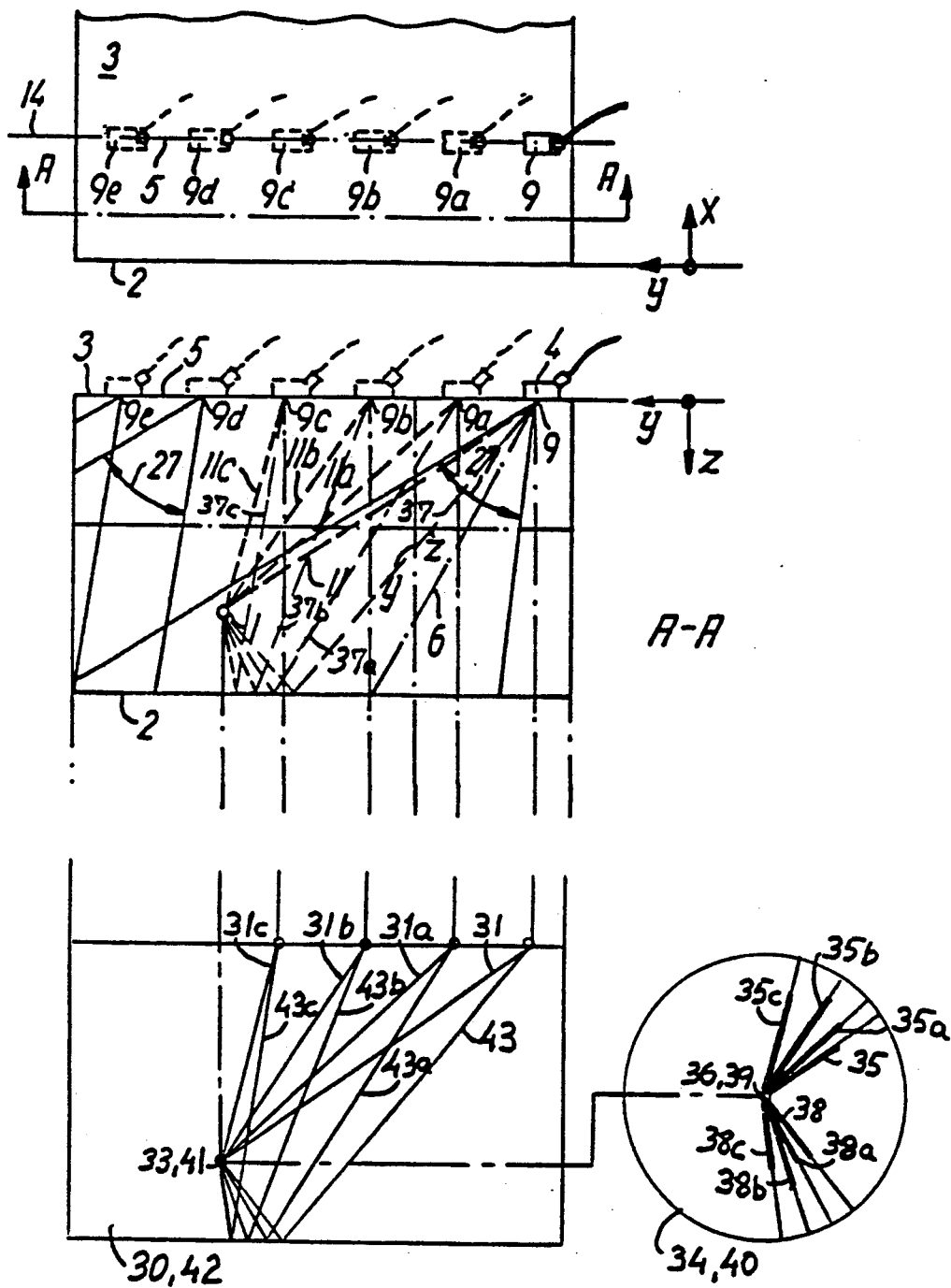
FIG. 4 is a schematic presentation of the addition to FIG. 3 of another sectional image according to the invention produced by echo pulses reflected from the back wall of the object.

FIG. 4 shows schematically a search for reflected echoes from the inhomogeneity 1 in accordance with the invention. For each distance 37,37a,37b,37c a search is carried out among the stored echo values, and if an echo is found at the distance searched for, it is displayed as a line segment 38,38a,38b,38c from the selected image pixel 39 in the sectional image 40, and the corresponding flaw image 41 is shown superimposed on the sectional image 42. The thin lines 31,31a,31b,31c and 43,43a, 43b,43c indicating the sound paths searched for may be retained for information during the phase of analysing the results of the examination.

Figure 5:
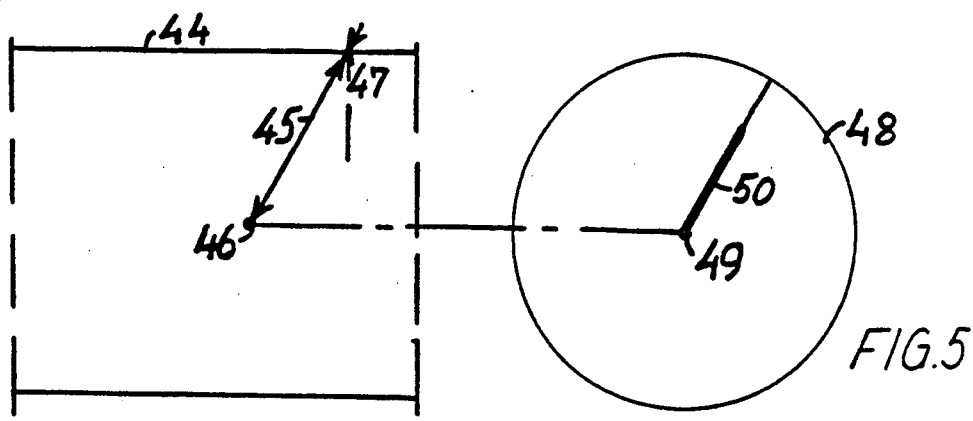
FIG. 5 is a schematic presentation of the production of an image according to the invention of a directly reflecting inhomogeneity.

FIG. 5 shows schematically a sectional view 44 of an ultrasonic pulse 45 transmitted from a first ultrasonic angle probe and reflected from an inhomogeneity 46 directly back to the point of incidence 47 of the ultrasonic beam from said ultrasonic probe. This is the first useful echo normally looked for, and shown in the separate sectional view 48 from the corresponding image pixel 49 as the line segment 50.

Figure 6:
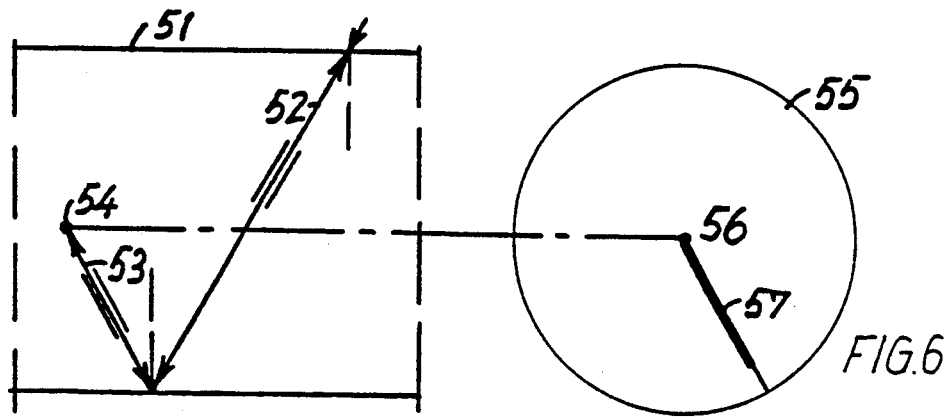
FIGS. 6 to 9 are similar schematic presentations of four possible indirect reflections of the inhomogeneity shown in FIG. 5.

FIG. 6 shows a sectional view 51 of an ultrasonic pulse 52 transmitted from a first ultrasonic angle probe as longitudinal waves which are first reflected as longitudinal waves 53 from the back wall of the object. Part of the waves are reflected from an inhomogeneity 54 back the same way to the ultrasonic probe. In the separate sectional view 55 from the corresponding image pixel 56 this reflected echo is shown as the line segment 57, and the flaw image 51 may then be superimposed on the image 44.

Figure 7:
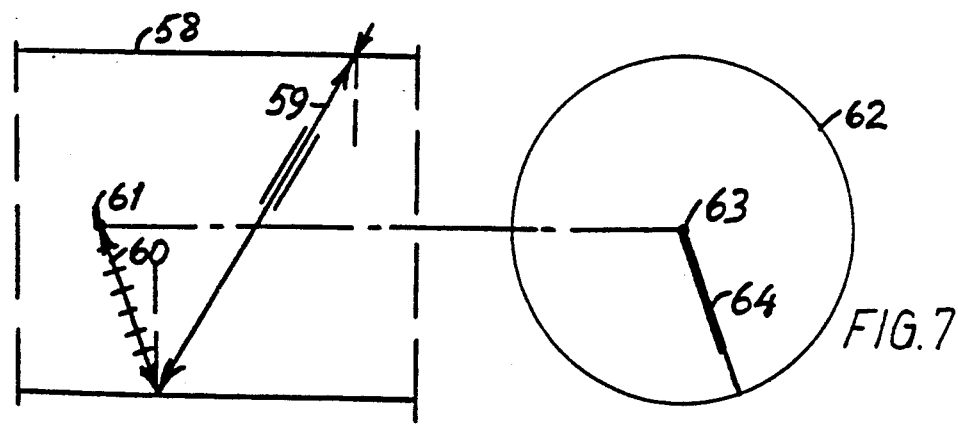

FIG. 7 shows a sectional view 58 of an ultrasonic pulse 59 transmitted from a first ultrasonic angle probe as longitudinal waves which are first reflected as transversal waves 60 from the back wall of the object. Part of the waves are reflected from an inhomogeneity 61 back the same way to the ultrasonic probe. In the separate sectional view 62 from the corresponding image pixel 63, this reflected echo is shown as the line segment 64, and the flaw image 58 may then be superimposed on the image 44.

Figure 8:
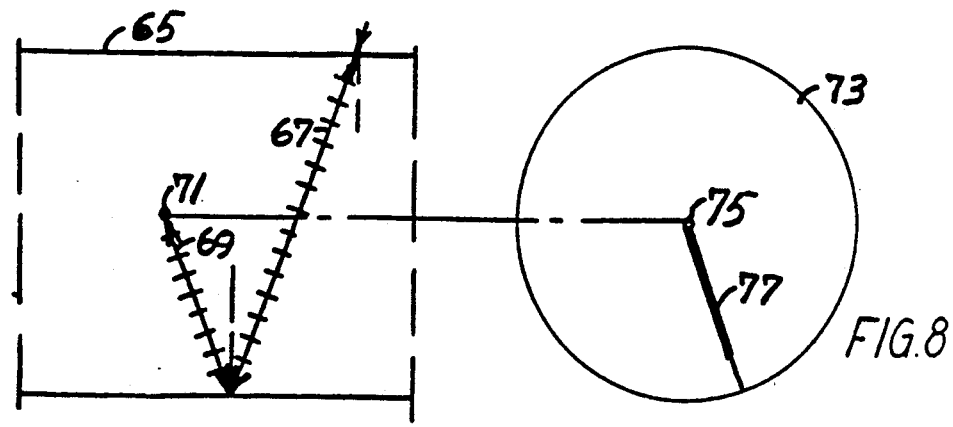
Figure 9:
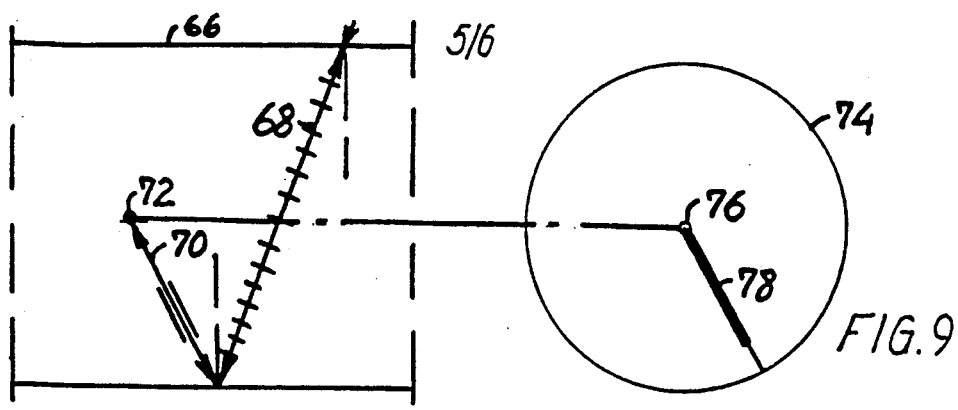

FIGS. 8 and 9 show sectional views 65,66 of ultrasonic pulses 67,68, transmitted from first ultrasonic angle probes as transversal waves which are reflected as transversal waves 69 or longitudinal waves 70 from the back wall of the object. Part of the waves are reflected from inhomogeneities 71,72 back the same way to the ultrasonic probe. In separate views 73,74 from corresponding image pixels 75,76, the reflected echoes are shown as line segments 77,78, and the flaw images 65,66 may then be superimposed on the image 44.

It is quite apparent, how the echo images may be a great help in the interpretation of the results of the examination, and equally apparent, how the flaw image 44 may be improved by adding the important information in the flaw images 54,61,71 and 72 which is disregarded in the prior art.

Figure 10:
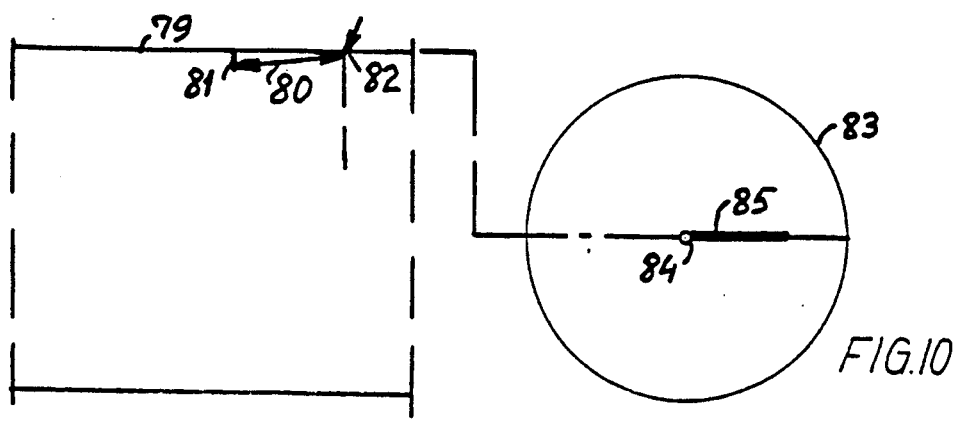
FIGS. 10 to 15 are similar schematic presentations of possible reflections when using a creep wave angle probe.

FIG. 10 shows a sectional view 79 of an ultrasonic pulse 80 transmitted from a first ultrasonic creep wave angle probe as creep waves reflected directly from a flaw 81 at or immediately below the surface of the object back to the point of incidence 82 of the sound beam from said ultrasonic probe. This is again a useful echo that is first looked for, and shown in the separate sectional view 83 from the corresponding image pixel 84 as a line segment 85.

Figure 11:
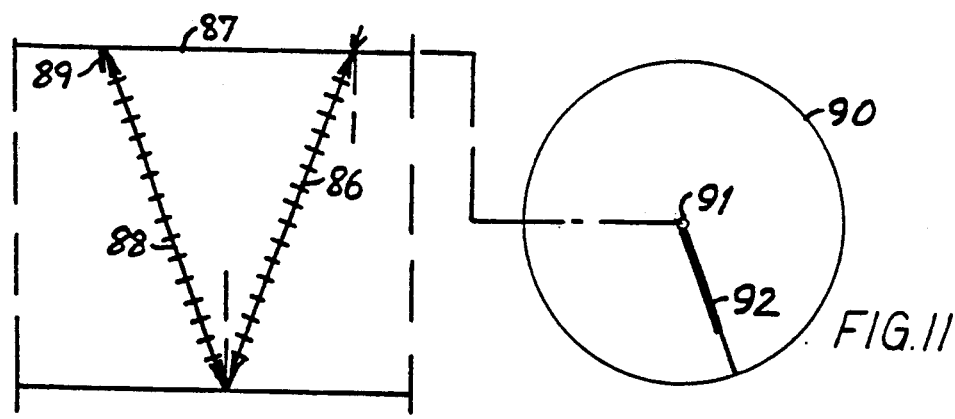

An ultrasonic creep wave angle probe also transmits secondary transversal waves 86 as shown in FIG. 11 which shows a sectional view 87 of an ultrasonic pulse of such transversal waves 88 from the back wall of the object. Part of the waves are reflected from the flaw 89 at or immediately below the surface of the object back to the ultrasonic probe. In the separate sectional view 90 from the corresponding image pixel 91 this reflected echo is shown as the line segment 92, and the flaw image 87 may then be superimposed on the image 79.

Figure 12:
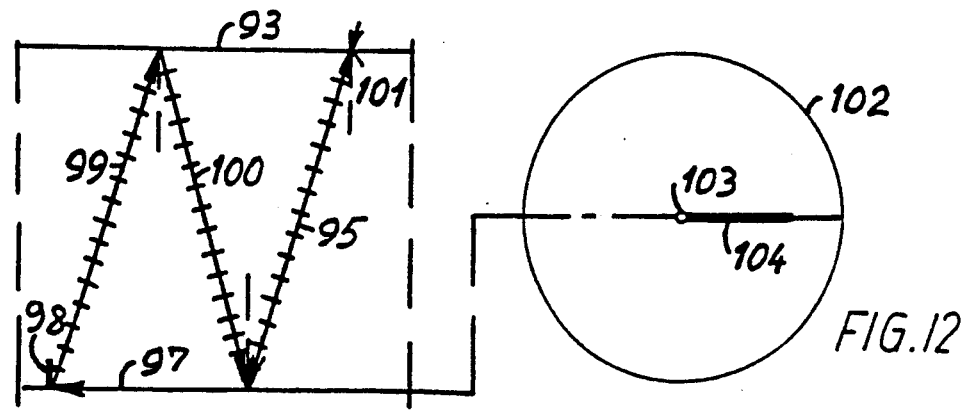
Figure 13:
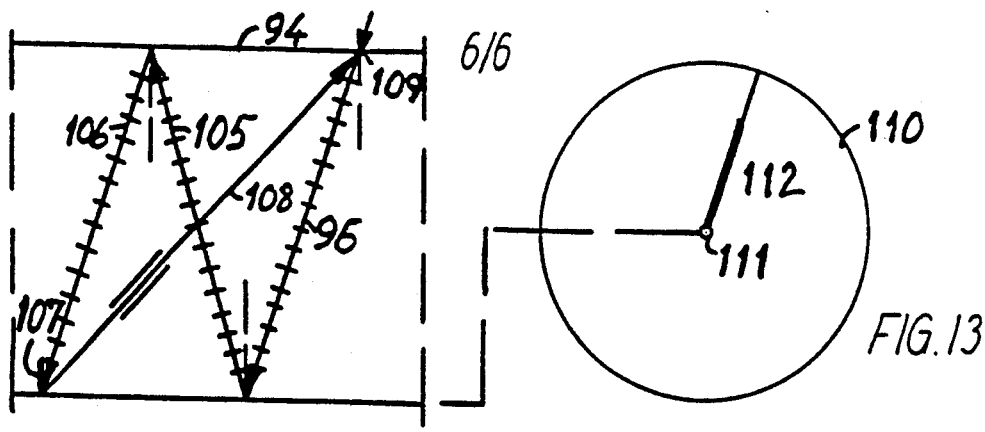

FIGS. 12 and 13 show sectional views 93 and 94, showing transversal waves 95 and 96, reflected in two different ways. In FIG. 12 the transversal wave 95 is changed into a creep wave 97. At the flaw 98 in the back surface, the wave is changed into a transversal wave 99 which is reflected at the front surface as a transversal wave 100 which is mirrored back to the point of incidence 101 of the sound beam. In the separate sectional view 102 from the corresponding image pixel 103, this reflected wave is shown as the line segment 104.

In FIG. 13 the transversal wave 96 is reflected twice as transversal waves 105 and 106 which at the flaw 107 are changed into a longitudinal wave 108 back to the point of incidence 109 of the sound beam. In the separate sectional view 110 from the corresponding image pixel 111, this reflected echo is shown as the line segment 112, and the flaw image 94 may then be superimposed on the flaw image 93.

Figure 14:
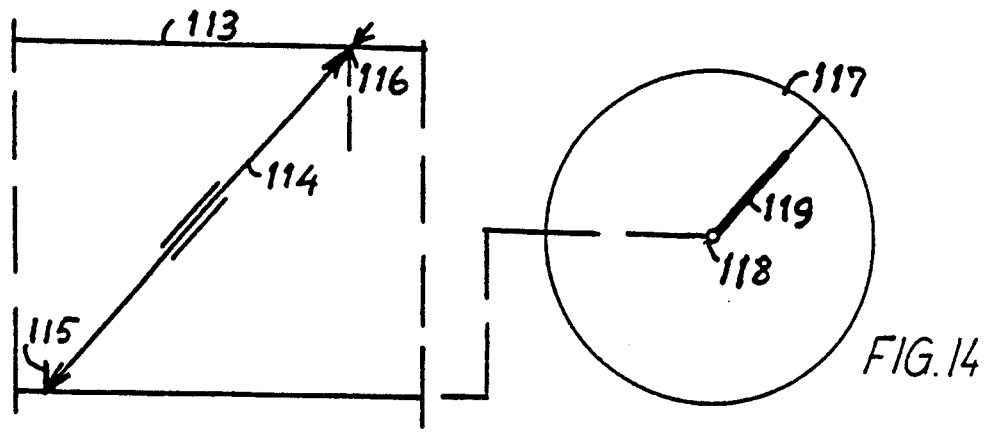

An ultrasonic creep wave angle probe also transmits secondary longitudinal waves as shown in FIG. 14 which shows a sectional view 113 of an ultrasonic pulse of such longitudinal waves 114 which are reflected back from the flaw 115 directly to the point of incidence 116 of the sound beam. In the separate sectional view 117 from the corresponding image pixel 118 this reflected echo is shown as the line segment 119, and the flaw image may again be superimposed on the flaw image 93.

Figure 15:
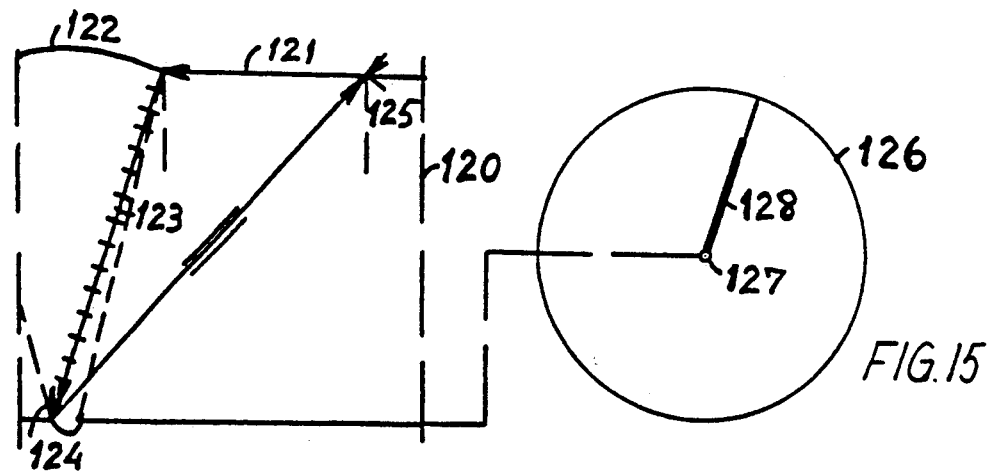

FIG. 15 shows in the sectional view 120, how creep waves 121 from a creep wave angle probe may be changed at the edge of a butt weld 122 into transversal waves 123. These waves are then reflected from a flaw 124 at or immediately below the back surface of the object back to the point of incidence 125 of the sound beam. In a separate sectional view 126 from the corresponding image pixel 127 the reflected waves are identified by the line segment 128.

Figure 16:
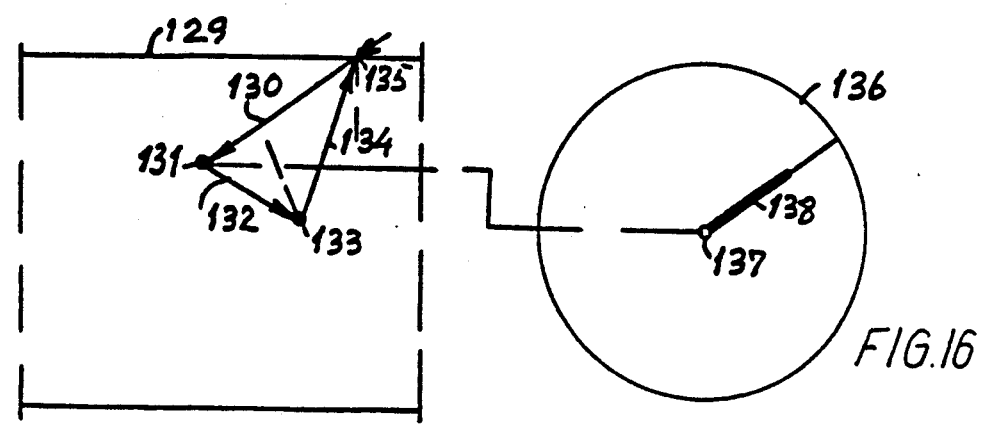
FIG. 16 is a schematic presentation according to the invention of a 'ghost reflection' from another inhomogeneity situated in the same sectional plane.

Finally FIG. 16 shows as an example in a sectional view 129, how an ultrasonic wave 130 from an ultrasonic angle probe may be reflected a first time from an inhomogeneity 131 as an ultrasonic wave 132, and then be reflected a second time from another inhomogeneity 133 as an ultrasonic wave 134 back to the point of incidence 135 of the sound beam. This false reflection is shown in the separate sectional view 136 from the corresponding image pixel 137 as the line segment 138. In this way it is possible to identify and disregard false, reflected echoes and their corresponding 'ghost images' in the sectional view 129.

It is clearly demonstrated in the examples above, how the amplitude line segments can be a very powerful tool, both on line during the examination, and in later post processing in the identification of reflected echoes and the disregarding of false echoes. At the same time the superimposing of the flaw images which may undergo the same methods of image enhancement and filtering as the direct image, may add important information which is disregarded in the prior art.

It will be understood that several modifications and variations of the method disclosed may be applied without departing from the spirit and scope of the novel concepts of the present invention.

We claim:

1. A method of visualizing reflection characteristics of reflecting inhomogeneities located by pulse-echo ultrasonic examination of an otherwise homogeneous object, said method comprising the steps of:

moving at least one ultrasonic probe over the surface of an object, the probe transmitting at predetermined intervals of time at least one short pulse of ultrasonic energy in the form of a sound beam with a central axis into the object and receiving echo pulses reflected from internal inhomogeneities;

storing, with a digital computing system, digital signals containing information on the corresponding, successive positions of the point of incidence and directions of the central axis of the sound beam and, on receipt of an echo pulse, information on the amplitude of the echo pulse and on the length of the sound path from the point of incidence to the reflecting point causing the echo pulse;

using the digital signals to display a first video flaw image of a sectional plane through the object;

displaying in at least one second separate video sectional image line segments representing the echo amplitudes, wherein the line segments have the length thereof representing the amplitude of the echoes and originate at the image pixel;

placing the chosen image pixel at the center of the image; and forming the line segments in the directions corresponding to the projections on the sectional plane of the incoming ultrasonic pulses at the location.

2. A method of visualizing reflection characteristics in ultrasonic examinations, said method comprising the steps of:

displaying the amplitude of echoes in the form of echo pulses resulting from the reflection of incoming ultrasonic energy by internal inhomogeneities as projections of spatial line segments drawn in the directions of projections on a freely selectable sectional plane of the incoming ultrasonic pulses at the point of reflection;

determining the spatial directions from which the individual reflected pulses have reached the point; and determining the percentage by which the individual echoes have contributed to the amplitude represented by the line segment.

3. A method of visualizing reflection characteristics, said method comprising the steps of:

moving an ultrasonic probe over the surface of an object so that the entire volume of the object has been insonified;

storing from ultrasonic examination, digital signals representing the successive positions of the point of incidence and the corresponding echo data and digital signals representing the corresponding directions of the central axis of the sound beam relative to the object;

selecting any sectional plane through the object and any image pixel in the corresponding video sectional image; and indicating, as projections of spatial line segments drawn in the directions of the projections on the sectional plane of the corresponding sound paths the amplitude of echoes displayed in the form of line segments drawn in the directions of projections on the selected sectional plane of the incoming ultrasonic pulses at the point of reflection.

4. The method of claim 3 further comprising selecting the various incoming ultrasonic pulses from the totality of information stored during said storing step by their various sound path lengths.

5. The method of claim 4 wherein said selecting step includes selecting the directly reflected sound path.

6. The method of claim 4 wherein said selecting step includes selecting the indirect sound paths reflected from the back wall of the object.

7. The method of claim 3 further comprising, by the amplitude line segments, illustrating and evaluating the corresponding echo amplitudes.

8. A method of visualizing reflection characteristics, said method comprising the steps of:

storing, from ultrasonic examination, digital signals representing the successive positions of the point of incidence and the corresponding echo data and digital signals representing the corresponding directions of the central axis of the sound beam, relative to an object;

selecting a sectional plane through the object;

selecting an image pixel in the video image of the sectional plane, to represent a chosen location inside the object; and displaying line segments representing the echo amplitudes, wherein the line segments have the lengths thereof representing the echo amplitudes, originate at the image pixel, and extend in the directions of the projections on the sectional plane of the incoming ultrasonic pulses at the location.

9. The method of claim 8 wherein the sectional plane is askew to all ultrasonic examination scanning lines.

10. The method of claim 8 wherein the sectional plane is at other than a right angle to the surface of the object.

11. The method of claim 8 wherein said displaying step includes drawing the line segments in the directions of the incoming ultrasonic pulses at the chosen location.

12. A method of visualizing reflection characteristics of reflecting inhomogeneities located by pulse-echo ultrasonic examination of an otherwise homogeneous object, where representatives of the several possible, individual echo amplitudes from a chosen location are shown as lengths of line segments originating at an image pixel representing said location in a video image of a sectional plane through the object, characterized in that:

said lengths of line segments are drawn in the directions of the projections on said sectional plane of the incoming ultrasonic pulses at said location.

13. Method according to claim 12, where at least one ultrasonic probe is moved over the surface of the object, transmitting at predetermined intervals of time at least one short pulse of ultrasonic energy into the object and receiving echo pulses from internal inhomogeneities, where digital computing means are adapted to store digital signals containing information on the corresponding, successive positions of the point of incidence and directions of the central axis of the sound beam, and, on receipt of an echo pulse, information on the amplitude of said echo pulse, and on the length of the sound path from said point of incidence to the reflecting point causing the echo pulse, and where said digital signals are used to display a video flaw image of a sectional plane through the object, characterised in that said line segments are shown superimposed on said video sectional flaw image.

14. Method according to claim 12, where at least one ultrasonic probe is moved over the surface of the object, transmitting at predetermined intervals of time at least one short pulse of ultrasonic energy into the object and receiving echo pulses from internal inhomogeneities, where digital computing means are adapted to store digital signals containing information on the corresponding, successive positions of the point of incidence and directions of the central axis of the sound beam, and, on receipt of an echo pulse, information on the amplitude of said echo pulse, and on the length of the sound path from said point of incidence to the reflecting point causing the echo pulse, and where said digital signals are used to display a first video flaw image of a sectional plane through the object, characterised in that said line segments are shown in at least one second separate video sectional image, where the chosen image pixel is placed at the centre of said image, and where said line segments are drawn in the directions corresponding to the projections on said sectional plane of the incoming ultrasonic pulses at said location.

15. Method according to claim 14, characterised in that the ultrasonic pulse transmitted by the ultrasonic probe is reflected back directly to the point of incidence of the sound beam from said ultrasonic probe.

16. Method according to claim 14, characterised in that the pulse transmitted from the ultrasonic probe consists of longitudinal waves which are first reflected as longitudinal waves from the back of the object, in that said waves are then reflected back the same way to said probe from an internal inhomogeneity, and, if the amplitude of the reflected waves exceeds a predetermined level, in that the sectional flaw image thus produced is shown superimposed on said first sectional flaw image.

17. Method according to claim 14, characterised in that the pulse transmitted from the ultrasonic probe consists of longitudinal waves which are first reflected as transversal waves from the back of the object, in that said waves are then reflected back the same way to said probe from an internal inhomogeneity, and, if the amplitude of the reflected waves exceeds a predetermined level, in that the sectional flaw image thus produced is shown superimposed on said first sectional flaw image.

18. Method according to claim 14, characterised in that the pulse transmitted from the ultrasonic probe consists of transversal waves which are first reflected as transversal waves from the back of the object, in that said waves are then reflected back the same way to said probe from an internal inhomogeneity, and, if the amplitude of the reflected waves exceeds a predetermined level, in that the sectional flaw image thus produced is shown superimposed on said first sectional flaw image.

19. Method according to claim 14, characterised in that the pulse transmitted from the ultrasonic probe consists of transversal waves which are first reflected as longitudinal waves from the back of the object, in that said waves are then reflected back the same way to said probe from an internal inhomogeneity, and, if the amplitude of the reflected waves exceeds a predetermined level, in that the sectional flaw image thus produced is shown superimposed on said first sectional flaw image.

20. Method according to claim 14, characterised in that the ultrasonic pulse transmitted from an ultrasonic creep wave angle probe is reflected back as a creep wave directly from a flaw at or immediately below the front surface of the object to the same ultrasonic probe.

21. Method according to claim 14, characterised in that the pulse transmitted from an ultrasonic creep wave angle probe consists of transversal waves which are first reflected as transversal waves from the back of the object, in that said waves are then reflected back the same way to said probe from a flaw at or immediately below the front surface of the object, and, if the amplitude of the reflected waves exceeds a predetermined level, in that the sectional flaw image thus produced is shown superimposed on said first sectional flaw image.

22. Method according to claim 14, characterised in that the ultrasonic pulse transmitted from an ultrasonic creep wave angle probe as transversal waves is changed at the back wall surface into creep waves which are reflected from a flaw at or immediately below said back wall surface as transversal waves which are reflected a second time from the front surface of the object and reflected a third time from the back wall as transversal waves which are finally received back at the point of incidence of said ultrasonic probe, and, if the amplitude of the reflected waves exceeds a predetermined level, in that the sectional flaw image thus produced is shown superimposed on said first sectional flaw image.

23. Method according to claim 14, characterised in that the ultrasonic pulse transmitted from an ultrasonic creep wave angle probe as transversal waves is first reflected as transversal waves back to the front surface, then reflected as transversal waves to the back wall surface, where a flaw at or immediately below said surface reflects the pulse as longitudinal waves which are finally received back at the point of incidence of said ultrasonic probe, and, if the amplitude of the reflected waves exceeds a predetermined level, in that the sectional flaw image thus produced is shown superimposed on said first sectional flaw image.

24. Method according to claim 14, characterised in that the ultrasonic pulse transmitted from an ultrasonic creep wave angle probe as longitudinal waves is reflected from a flaw at or immediately below the back wall surface as longitudinal waves directly back to the point of incidence of said ultrasonic probe, and, if the amplitude of the reflected waves exceeds a predetermined level, in that the sectional flaw image thus produced is shown superimposed on said first sectional flaw image.

25. Method according to claim 14, characterised in that the ultrasonic pulse transmitted from an ultrasonic creep wave angle probe as creep waves along the front surface of the object is changed at the edge of a butt weld into transversal waves which are reflected from a flaw at or immediately below the back wall surface as longitudinal waves which are finally received back at the point of incidence of said ultrasonic probe, and, if the amplitude of the reflected waves exceeds a predetermined level, in that the sectional image thus produced is shown superimposed on said first sectional flaw image.

26. Method according to claim 14, characterised in that the ultrasonic pulse transmitted by an ultrasonic probe is first reflected by a first internal inhomogeneity, reflected a second time from a second internal inhomogeneity, and finally received back at the point of incidence of said ultrasonic angle probe.

* * * * *